United States Patent
Xu et al.

(10) Patent No.: US 9,598,704 B2
(45) Date of Patent: Mar. 21, 2017

(54) INKJET GENE PRINTING

(71) Applicant: Wake Forest University Health Sciences, Winston-Salem, NC (US)

(72) Inventors: Tao Xu, El Paso, TX (US); James J. Yoo, Winston-Salem, NC (US); Anthony Atala, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 0 days.

(21) Appl. No.: 14/697,704

(22) Filed: Apr. 28, 2015

(65) Prior Publication Data

US 2015/0299730 A1   Oct. 22, 2015

Related U.S. Application Data

(62) Division of application No. 12/663,020, filed as application No. PCT/US2008/007158 on Jun. 6, 2008, now Pat. No. 9,045,757.

(60) Provisional application No. 60/942,549, filed on Jun. 7, 2007.

(51) Int. Cl.
| C12N 15/87 | (2006.01) |
| C12N 5/00  | (2006.01) |
| C12N 15/63 | (2006.01) |
| C12N 15/89 | (2006.01) |
| A61K 31/713 | (2006.01) |

(52) U.S. Cl.
CPC .......... *C12N 15/895* (2013.01); *A61K 31/713* (2013.01); *C12N 15/63* (2013.01); *C12N 15/87* (2013.01); *C12N 15/89* (2013.01)

(58) Field of Classification Search
CPC ...... A61K 31/713; C12N 15/63; C12N 15/87; C12N 15/89; C12N 15/895
USPC ..................... 435/455; 506/26, 40; 514/44 R
See application file for complete search history.

(56) References Cited

U.S. PATENT DOCUMENTS

| 4,945,050 A | 7/1990 | Sanford et al. |
| 5,122,466 A | 6/1992 | Stomp et al. |
| 5,518,909 A | 5/1996 | Banes |
| 5,580,859 A | 12/1996 | Felgner et al. |
| 6,652,878 B2 | 11/2003 | Webb et al. |
| 7,051,654 B2 * | 5/2006 | Boland ............ B01L 3/0268 101/483 |
| 7,105,347 B2 | 9/2006 | Fang et al. |
| 2004/0237822 A1 | 12/2004 | Boland et al. |

FOREIGN PATENT DOCUMENTS

WO   WO 2004/108418 A1   12/2004

OTHER PUBLICATIONS

Xu et al. (2006, Biomaterials vol. 27, pp. 3580-3588).*
Castel et al. (2007 Drug discovery today, vol. 11, pp. 616-622).*
Waldman et al. Analytical Biochemistry, vol. 258, No. 2, 1998, 216-222.*
Clarke et al. Journal of Cell Science, vol. 102, No. 3, 1992, 533-541.*
Xu T et al. Viability and electrophysiology of neural cell structures generated by the inkjet printing method. Biomaterials. 2006; 27: 3580-3588.
Castel et al. Cell microarrays in drug discovery. Drug Discovery Today. Jul. 2006; 11(13/14); 616-622.
International Search Report, PCT/US2008/007158, mailed Dec. 29, 2008.
Xu T et al. Inkjet printing of viable mammalian cells. Biomaterials. 2005; 26: 93-99.
Boland T et al. Application of inkjet printing to tissue engineering. Biotechnol. J. 2006; 1: 910-917.
Castel D et al. Cell microarrays in drug discovery. Drug Discovery Today. Jul. 2006; 11: 616-622.
Ringeisen BR et al. Jet-based methods to print living cells. Biotechnol. J. 2006; 1: 930-948.
Yang N-S et al. In vivo and in vitro gene transfer to mammalian somatic cells by particle bombardment. Proc. Natl. Acad. Sci. USA, Dec. 1990; 87: 9568-9572.
Harris TM et al. Injecting new ideas into microarray printing. Nature Biotechnology. Apr. 2000; 18: 384-385.
Okamoto T et al. Microarray fabrication with covalent attachment of DNA using Bubble Jet technology. Nature Biotechnology. Apr. 2000; 18: 438-441.
Calvert P. Inkjet printing for materials and devices. Chem. Mater. 2001; 13: 3299-3305.
Boland T et al. Cell and organ printing 2: fusion of cell aggregates in three-dimensional gels. The Anatomical Record Part A. 2003; 272A: 497-502.
Pardo L et al. Characterization of patterned self-assembled monolayers and protein arrays generated by the ink-jet method. Langmuir. 2003; 19: 1462-1466.
Wilson WC, JR and Boland T. Cell and organ printing 1: protein and cell printers. The Anatomical Record Part A. 2003; 272A: 491-496.
Jakab K et al. Engineering biological structures of prescribed shape using self-assembling multicellular systems. PNAS, Mar. 2, 2004; 101(9): 2864-2869.
Xu T et al. Construction of high-density bacterial colony arrays and patterns by the ink-jet method. Biotechnology and Bioengineering. Jan. 5, 2004; 85(1): 29-33.
The nucleofector technology—a revolution in transfection. Amaxa Biosystems product description. 2007: 1 page.

(Continued)

*Primary Examiner* — Janet Epps-Smith
(74) *Attorney, Agent, or Firm* — Myers Bigel, P.A.

(57) ABSTRACT

Provided herein are methods and apparatuses for transfecting a cell with a compound of interest by stressing the cell, e.g. with shear stress. The compound of interest may be nucleic acids, proteins, molecules, nanoparticles, drugs, etc., or any combination thereof. Methods of printing cells with an inkjet printing device are also provided, wherein at least a portion of viable cells (preferably at least 1%) are transfected with a compound of interest. Preferably, at least 25% of the cells are viable after printing. In addition, methods of forming an array of viable cells are provided wherein at least a portion of the viable printed cells (preferably at least 1%) are transfected with at least one compound of interest.

37 Claims, 5 Drawing Sheets

(56) References Cited

OTHER PUBLICATIONS

How inkjet printers work. howstuffworks.com. 2007: 3 pp.
Xu T et al. Inkjet gene printing: a novel approach to achieve gene modified cells for tissue engineering. Conference Paper. Proceedings of the Army Science Conference (26th). Orlando, FL. Dec. 2008: 9 pp.
Bailey SN et al. Applications of transfected cell microarrays in high-throughput drug discovery. Drug Discovery Today. 2002; 7(18) Suppl.: S113-S118.
Azzam T and Domb AJ. Current developments in gene transfection agents. Current Drug Delivery. 2004; 1(2): 165-193.
Fujiwara T et al. Impact of convective flow on the cellular uptake and transfection activity of lipoplex and adenovirus. Bio. Pharm. Bull. 2006; 29(7): 1511-1515.
Zarnitsyn VG et al. Electrosonic ejector microarray for drug and gene delivery. Biomed Microdevices. 2008; 10: 299-308.
Xu T et al. Inkjet-mediated gene transfection into living cells combined with targeted delivery. Tissue Engineering : Part A. 2009; 15(1): 95-101.
Supplementary European Search Report, EP 08768231, mailed Jul. 30, 2010.
European Communication Corresponding to Application No. 08 768 231.6-2403; Dated May 19, 2011; 8 Pages.
Clarke M S F et al: "Syringe Loading Introduces Macromolecules Into Living Mammalian Cell Cytosol", *Journal of Cell Science*, vol. 102, No. 3, 1992, pp. 533-541, XP007918572, ISSN: 0021-9533.
Waldman A S et al: "Stable Transfection of Mammalian Cells by Syringe-Mediated Mechanical Loading of DNA", *Analytical Biochemistry*, Academic Press Inc, New York, vol. 258, No. 2, May 1, 1998, pp. 216-222, XP002172199, ISSN: 0003-2697.

McNeil P L: "Direct Introduction of Molecules Into Cells", *Current Protocols in Cell Biology/Editorial Board*, Juan S. Bonifacino, et al., May 2001 LNKD-PUBMED:18228351, vol. Chapter 20, May 2001 (May 2001), XP007918571, ISSN: 1934-2616.
Clarke Mark S F et al: "Syringe Loading: A Method for Inserting Macromolecules Into Cells in Suspension" *Cell Biology*, vol. 4. Second Edition, 1998, Academic Press, Inc., 1250 Sixth Ave., San Diego, California 92101, USA; Academic Press Ltd., 14 Belgrave Square, 24-28 Oval Road, London NW1 7OX, England, UK, XP009148142, ISBN: 0-12-164729-3. vol. 4, pp. 49-54.
Office Action, Chinese Patent Application No. 200880102309.4, Oct. 17, 2011, 8 pp.
Examination Report, EP 08768231.6, May 5, 2011; response thereto on Sep. 23, 2011.
Examination Report, EP 08768231.6, Jun. 27, 2012; response thereto on Nov. 21, 2012.
Eraizer TL; Lazarevich NL. Transfection by point pressure: Rapid and efficient method for Incorporation of macromolecules into mammalian cells. Molekulyarnaya Biologiya (Moscow). 1996, vol. 30, No. 2, pp. 426-431, English abstract unavailable.
Mann MJ et al. Pressure-mediated oligonucleotide transfection of rat and human cardiovascular tissues. PNAS USA. May 1999; 96: 6411-6416.
Wells DJ. Gene therapy progress and prospects: electroporation and other physical methods. Gene Therapy. 2004; 11: 1363-1369.
Mehier-Humbert S and Guy RH. Physical methods for gene transfer: improving the kinetics of gene delivery into cells. Advanced Drug Delivery Reviews. 2005; 57: 733-753.
Examination Report, Japanese Patent Application No. 2010-511208, dispatched Aug. 6, 2013, and English summary.
Examination Report, EP 08768231.6, mailed Apr. 8, 2013.
Response to Examination Report, EP 08768231.6, Aug. 13, 2013.

* cited by examiner

INKJET GENE PRINTING

RELATED APPLICATIONS

This application is a divisional application of U.S. patent application Ser. No. 12/663,020, filed Feb. 3, 2010, now U.S. Pat. No. 9,045,757, which is a 35 U.S.C. §371 national phase entry of PCT Application No. PCT/US2008/007158, filed Jun. 6, 2008, which claims the benefit of U.S. Provisional Patent Application Ser. No. 60/942,549, filed Jun. 7, 2007, the disclosure of each of which is incorporated herein by reference in its entirety.

FIELD OF THE INVENTION

The present invention concerns the delivery of compounds of interest into living cells.

BACKGROUND OF THE INVENTION

In the interdisciplinary field of tissue engineering, powerful new therapies are being developed to address structural and functional disorders of human health by utilizing living cells as engineering materials. See Viola et al., "The Emergence of Tissue Engineering as a Research Field," prepared for the National Science Foundation, Oct. 14, 2003, available at nsf.gov. In some areas of tissue engineering, researchers are creating two- and three-dimensional tissues and organs from combinations of cells in order to repair or replace diseased or damaged tissues.

In instances where normal tissue cannot be engineered with the available cells, or enhanced cellular function is required, alternative approaches such as growth factor supplementation, macromolecule treatment or gene modification may be necessary to achieve the desired functionality. Moreover, in tissue engineering, the transfection or delivery of genes, proteins, molecules, nanoparticles, drugs, etc. is becoming vital in order to facilitate the formation of functional tissues and organs.

Gene transfection techniques have been used in various areas of research to improve cell and tissue function. Although there are established methods in the art for delivering genes into cells, the application of existing techniques to tissue engineering is not ideal. An important goal in gene transfection is to achieve efficient gene delivery to a target cell population while preserving cell viability. Currently, the most widely used methods for gene transfection are viral transfection, microinjection, electroporation, and the gene gun.

Transfection using viral vectors is a technique in which nucleic acids to be delivered are inserted into a virus. The nucleic acids are transported into the nucleus after the viral carriers enter the targeted cells by docking mechanisms. Although viral transfection has a high efficiency rate, it also has many drawbacks, such as residual pathogenicity, host immune response, and the potential induction of neoplastic growth following insertional mutagenesis. These concerns have restricted its application in medicine and in the biomedical areas, especially in clinical gene therapy.

Microinjection is another available technique. Genetic materials can be injected directly into cultured cells or nuclei by using microinjection needles. It is very effective in transferring specific genetic materials into the cells, and has been widely used in stem cell nuclear transfer applications. However, it is not efficient and not appropriate for studies and applications that require a significant number of cells to become transfected.

Electroporation, the application of controlled electric fields to facilitate cell permeabilization, is also used to enhance gene uptake into cells. The mechanism for entry is based upon perturbation of the cell membrane by an electrical pulse, which forms pores that allow the passage of the DNA. This technique requires optimization for the duration and strength of the pulse for each type of cell used, and requires a critical balance between allowing efficient delivery and killing cells. Low cell viability is a major limitation of transfection by electroporation.

Finally, the gene gun can achieve direct gene delivery into tissues or cells by shooting gold particles coated with DNA at the cells. This technique allows direct penetration through the cell membrane into the cytoplasm and even the nucleus, bypassing the endosomal compartment of the cell. However, this method is limited by a low transfection efficiency.

Therefore, there is a need for new methods to effectively and efficiently transfect cells with nucleic acids, proteins, molecules, nanoparticles, drugs, etc. while protecting their viability. There is also a need to combine transfection with cell delivery, and further to combine these techniques into one platform or device for efficient and effective transfection in tissue engineering applications.

SUMMARY OF THE INVENTION

In one aspect of the invention, methods are provided for transfecting cells with a compound of interest, comprising: 1) providing a composition comprising the compound of interest and the cells in a liquid carrier; and 2) forcing said composition through an orifice so that the cells are stressed in the presence of the compound of interest. In some embodiments, at least 1% of viable cells are transfected (e.g., by count, comparing the number of viable transfected cells with the total number of viable cells (transfected and non-transfected)). In some embodiments, the forcing step is carried out for a time of 1 to 100 microseconds. In some embodiments, the cells are eukaryotic or prokaryotic cells, and the compound of interest is selected from the group consisting of: nucleic acids, proteins, molecules, nanoparticles and drugs. In further embodiments, the forcing step is carried out by inkjet printing of the cells with an inkjet printing device.

In another aspect of the invention, methods of printing cells are provided, wherein at least a portion of the cells are transfected with a compound of interest, comprising the steps of: 1) providing an inkjet printing device comprising at least one inkjet printer cartridge; 2) loading a composition to be printed into the printer cartridge(s), such that the composition upon loading comprises the cells in the presence of the compound of interest; and 3) printing said loaded composition onto a substrate. In some embodiments, the substrate is coated, e.g., with agar or collagen. In other embodiments, the composition is printed onto a tissue substrate in vivo. Preferably, at least 1% of viable printed cells are transfected (e.g., by count, comparing the number of viable transfected cells with the total number of viable cells (transfected and non-transfected)), and at least 25% of the printed cells are viable subsequent to printing (comparing the total number of viable cells prior to printing with the total number of viable cells subsequent to printing). Cells that may be printed include eukaryotic and prokaryotic cells, and compounds of interest include nucleic acids, proteins, molecules, nanoparticles and drugs.

A further aspect of the invention is methods of forming an array of viable cells comprising: 1) providing an inkjet printing device comprising at least one inkjet printer cartridge; 2) loading a composition into the printer cartridge(s), such that the composition comprises cells in the presence of at least one compound of interest; and 3) printing the composition onto a substrate in an organized pattern. In some embodiments, the substrate is coated, e.g., with agar or collagen. In other embodiments, the composition is printed onto a tissue substrate in vivo. Preferably, at least 1% of viable printed cells are transfected (e.g., by count, comparing the number of viable transfected cells with the total number of viable cells (transfected and non-transfected)), and at least 25% of printed cells are viable subsequent to said printing step (comparing the total number of viable cells prior to printing with the total number of viable cells subsequent to printing). Cells that may be printed include eukaryotic and prokaryotic cells, and compounds of interest include nucleic acids, proteins, molecules, nanoparticles and drugs.

Also provided is an apparatus for printing cells that included an inkjet printing device having at least one inkjet printer cartridge and a composition to be printed that is loaded into the printer cartridge(s), the composition including cells in the presence of at least one compound of interest.

Another aspect of the present invention is the use of the methods as described herein for the preparation of a composition or medicament for use in treatment or for carrying out a method of treatment as described herein, or for making an article of manufacture as described herein.

BRIEF DESCRIPTION OF THE DRAWINGS

(FIGS. 2A-2C) Morphologies of the transfected cells. The PAEC cells exhibited normal morphologies on the collagen gels 2 days after printing (FIG. 2A). GFP expression was seen among these printed cells under GFP fluorescent microscopy (FIG. 2B). The nuclei of the printed cells (lighter spots) and the gene expression of the transfected cells (brighter spots) were both seen with DAPI and GFP fluorescent microscopy (FIG. 2C). (FIGS. 2D and 2E) Comparison of the inkjet transfection method with a liposome-based method and electroporation method. Compared with the liposome chemical (Lipofectamine™ 2000 reagent) or electroporation (Nucleofection) methods, the inkjet transfection method had higher cell viability after transfection (FIG. 2D). The total transfection efficiency of the inkjet method is lower than that of the Nucleofection method, but higher than the Lipofectamine™ reagent method (FIG. 2E). (FIG. 2F-2H) Effects of the printing parameters and conditions on gene transfection. The plasmids at higher concentrations exhibited a higher transfection efficiency (FIG. 2F). The HP 51629a ("HP 29") ink cartridge (smaller nozzle diameter) exhibited higher gene expression than the HP 51626a ("HP 26") cartridge (larger nozzle diameter) (FIG. 2G). Compared to the larger pIRES plasmids containing lacZ and GFP-VEGF, the smaller pmaxGFP™ plasmid exhibited a higher transfection efficiency (FIG. 2H).

(FIG. 7A) Retrieval of the implant from the subcutaneous tissues of the nude mouse after 1-week implantation. The in situ fabricated fibrin sheet was seen in the subcutaneous tissues of the mouse, and vasculature was found in the fibrin sheet. (FIG. 7B) Gross examination of the retrieved fibrin sheet in the culture dish. The fibrin gel exhibited the rectangle shape, which matches up with the pre-designed pattern for the in situ direct printing. (FIGS. 7C and 7D) Fluorescent microscopy of the cells within the fibrin sheet. The nuclei of the cells within the fibrin sheet were not only seen in DAPI blue (lighter spots), but also GFP expression (brighter spots) was found among the cells entrapped within the fibrin sheet (FIG. 7C). The transfected cells also exhibited red fluorescence (brighter spots in FIG. 7D), which indicates that the transfected cells were the grafted cells from the in vivo direct inkjet printing (FIG. 7D).

DETAILED DESCRIPTION OF THE PREFERRED EMBODIMENTS

Figure 1:
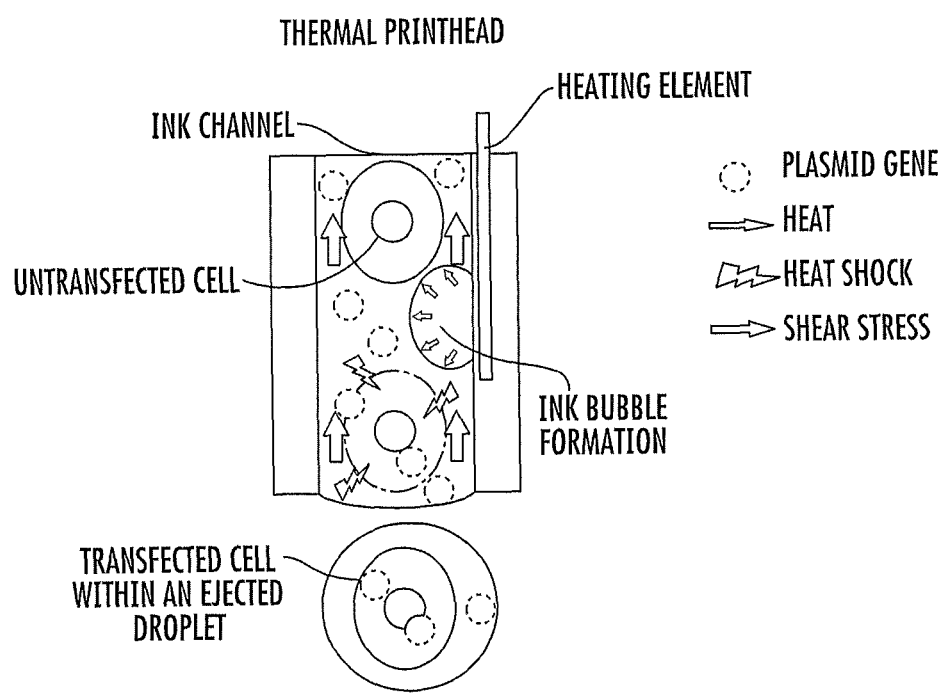
FIG. 1. Schematic drawing of the potential mechanism of gene transfection by co-printing. When cells and plasmid vectors pass the ink channels of the print head during the printing process, the high shear stress and heat occurring upon the nozzle firing may cause a temporary micro-disruption of the cell membrane, allowing the plasmids to be transferred into the cells.

The present invention is directed to methods of transfecting compounds of interest into viable cells. The disclosures of all cited U.S. patent references are hereby incorporated by reference to the extent they are consistent with the disclosure herein.

As used herein in the description of the invention and the appended claims, the singular forms "a," "an" and "the" are intended to include the plural forms as well, unless the context clearly indicates otherwise. Furthermore, the terms "about" and "approximately" as used herein when referring to a measurable value such as an amount of a compound, dose, time, temperature, and the like, is meant to encompass variations of 20%, 10%, 5%, 1%, 0.5%, or even 0.1% of the specified amount. Also, as used herein, "and/or" refers to and encompasses any and all possible combinations of one or more of the associated listed items, as well as the lack of combinations when interpreted in the alternative ("or").

"Transfection" or "transformation" as used herein refers to the delivery of a compound of interest into a cell. For simplicity, the term "transfection" is used herein with regard to both eukaryotic and prokaryotic cells. "Compound of interest" includes, but is not limited to, compounds comprising nucleic acids (e.g., genes, plasmids, siRNA, etc.), proteins, small molecules, nanoparticles (i.e., a microscopic particle with at least one dimension less than 200 nm), drugs, or other compounds that are to be delivered into a viable cell. In some embodiments, the compound of interest is included in a composition that also includes the cell or cells to be transfected. Ideal concentrations of compounds of interest in the composition may be determined empirically. Concentrations of compounds of interest in the composition used according to some embodiments include, but are not limited to, from 0.01 to 50 µg/µL, 0.05 to 10, 15 or 20 µg/µL, 0.1 to 5 µg/µL, 0.1 to 2.0 µg/µL, and 1 to 2 µg/µL of the composition. Ideal concentrations of cells may also be determined empirically, taking into account the relative sizes of various cell types. Concentrations of cells in the composition according to some embodiments include, but are not limited to, approximately $10^5$, $10^6$, $10^7$, $10^8$ or $10^9$ cells/mL.

In some embodiments, compounds of interest are provided in a vector (i.e., vehicles for delivery). Any suitable vector may be used, including, but are not limited to, nucleic acid vectors, liposome-based (e.g., cationic lipid) vectors, such as quaternary ammonium detergents, cationic derivatives of cholesterol and diacylglycerol, and lipid derivatives of polyamines; peptide-based vectors, such as Cys-Trp-Lys, etc.; polymer-mediated vectors, such as polyethylenimines (PEI), biodegradable polymers (e.g., poly[a-(4-aminobutyl)-L-glycolic acid]), thermo-sensitive polymers (e.g., poly(N-isopropylacrylamide (IPAAm)-co-2-(dimethylamino)ethyl methacrylate (DMAEMA)-co-butylmethacrylate (BMA)), PEG-poly(D,Llacticacid-co-glycolic acid)); diethylaminoethyl (DEAE)-dextran; calcium phosphate; activated Dendrimers; non-liposomal lipids; and functional nanoparticles, such as Quantum-dot nanoparticles, gold nanoparticles, silica nanoparticles, magnetic nanoparticles, lipid nanoparticles, polycationic nanoparticles, polymeric nanoparticles, etc.

Examples of common nucleic acid vectors include, but are not limited to, plasmids, cosmids, bacteriophages, DNA viruses, RNA viruses and retroviruses, all of which are known for the expression of a heterologous nucleic acid in cells. See, e.g., U.S. Pat. Nos. 6,392,118, 6,309,883, 6,258,354 and 4,959,313. The vector should include a suitable promoter (e.g., an SV40 promoter, retrovirus LTR-promoter, or cytomegalovirus (CMV) promoter), operatively associated with the nucleic acid to express one or more coding regions in the cells. Examples of plasmids that may be used according to some embodiments include, but are not limited to, pmaxGFP™ (Amaxa Biosystems, Gaithersburg, Md.), pIRES-VEGF-GFP (BD Biosciences, Bedford, Mass.), pIRES-lacZ (BCCM/LMBP, Belgium), and pMACSK$^K$II-PDX (Miltenyi Biotec, Germany). In some embodiments, the coding regions include a reporter gene such as green fluorescent protein (GFP) and/or a functional gene such as a growth factor (e.g., vascular endothelial growth factor (VEGF)) or differentiation factor. See, e.g., U.S. Patent Application Publication No. 2007/0031384, incorporated by reference herein. Nucleic acids may also be provided naked or complexed to cationic lipids. See, e.g., U.S. Pat. Nos. 5,676,954, 5,589,466, 5,693,622, 5,580,859, 5,703,055 and 6,413,942.

Expression of a nucleic acid may be stable expression or transient expression depending upon the specific system chosen. By the term "express" or "expression" of a nucleic acid coding sequence, it is meant that the sequence is transcribed, and optionally, translated. Typically, according to the present invention, expression of a coding region will result in production of the encoded polypeptide.

Compounds of interest may be provided in a liquid carrier in some embodiments. Examples of liquid carriers include, but are not limited to, water, an aqueous solution (e.g., phosphate buffered saline (PBS)), a transfection solution such as Nucleofector™ solution (Amaxa Biosystems, Gaithersburg, Md.), and so forth, and may include additional ingredients as desired.

Cells may be provided "in the presence of" compounds of interest. As used herein, cells are "in the presence of" compounds of interest when cells and compounds of interest are contained in the same composition, and the compounds of interest are physically outside of, but able to interact with, the cells, by diffusion or otherwise, e.g., prior to transfection. Cells in the presence of compounds of interest may or may not have been previously transfected with the same or different compounds of interest prior to transfection using the methods disclosed herein. In some embodiments compounds and/or compositions may be premixed to form a composition that includes both the compounds of interest and the cells. In other embodiments compounds of interest can be added to a composition containing cells just prior to transfection to form a composition that included both the compounds of interest and the cells.

"Cell" or "cells" as used herein may be any type of eukaryotic or prokaryotic cell, without limitation. Mammalian cells (including mouse, rat, dog, cat, monkey and human cells) are in some embodiments preferred, e.g., for tissue engineering applications. In applications where tissues produced by the processes herein are implanted in a subject, in some embodiments cells are of the same species as the subject into which the tissue is to be implanted. In some embodiments cells include those that are autogeneic (i.e., from the subject to be treated), isogeneic (i.e., a genetically identical but different subject, e.g., from an identical twin), allogeneic (i.e., from a non-genetically identical member of the same species) or xenogeneic (i.e., from a member of a different species). In some embodiments eukaryotic cells may be obtained from a donor (either living or cadaveric) or from an established cell line. To obtain cells from a donor (e.g., a potential recipient of a bioscaffold graft), standard biopsy techniques known in the art may be employed.

Examples of eukaryotic cells that may be transfected using the methods herein include, but are not limited to, mammalian cells, including stem cells, progenitor cells and differentiated cells, without limitation. Stem cells have the ability to replicate through numerous population doublings (e.g., at least 60-80), in some cases essentially indefinitely, and also have the ability to differentiate into multiple cell types (e.g., is pluripotent or multipotent). It is also possible for cells to be transfected with a compound of interest that results in the cells becoming immortalized (i.e., able to double more than 50 times). For example, it has been reported that mammalian cell transfection with telomerase reverse transcriptase (hTERT) can immortalize neural progenitor cells (See U.S. Pat. No. 7,150,989 to Goldman et al.).

Some cell types are very sensitive to harsh transfection techniques such as electroporation or liposome based transfection. For example, recently we have found that human amniotic fluid stem cells (AFS), after transfection with electroporation or liposome based agents, will typically stop growth and go through apoptosis. According to some embodiments of the invention, transfection as taught herein does not have significant effects on the viability, proliferation, and basic functions of more sensitive cells such as AFS cells.

In some embodiments, cells are provided in a liquid carrier. The liquid carrier can be in the form of a suspension, solution, or any suitable form. Examples of liquid carriers include, but are not limited to, water, aqueous solutions (e.g., phosphate buffer solution, citrate buffer solution, etc.), liquid media (e.g., modified Eagle's medium ("MEM"), Hanks' Balanced Salts, etc.), gels, and so forth, and may include additional ingredients as desired. In some embodiments, the use of a liquid carrier in the cell composition can ensure adequate hydration and minimize evaporation after printing. However, in some embodiments, the probability of obtaining viable cells in any given printed drop also decreases with decreasing cell concentration. See U.S. Pat. No. 7,051,654 to Boland et al.

In some embodiments the transfection may be carried out by "stressing" the cells, e.g., with tensile or shear stress, or compression or inertial loading or fluid movement. In some embodiments, stress may be normal stress or shear stress. In normal stress, the stress is perpendicular to the face of the material. Shear stress ("τ") refers to a stress state wherein the stress (e.g., friction) is substantially parallel or tangential to a face of the material (e.g., a cell membrane). In some embodiments, the cells are forced through an orifice such that the cells undergo shear stress. In some embodiments, the shear stress is from 0.5 to 500 $ms^{-1}$, or from 1 to 100 $ms^{-1}$, or from 5 and 15 $ms^{-1}$. In some embodiments, the cells are stressed for a limited period of time e.g., from $10^{-5}$ to $10^{-7}$ seconds. In some embodiments, the limited period of time is from 0.5 to 10 microseconds.

The ideal size of the orifice will depend upon the types of cells intended to be transfected. As a general guide, eukaryotic animal cells and plant cells are typically from 10 to 100 μm, and prokaryotic cells are typically from 0.1 to 10 μm in diameter. Before printing, in some embodiments the cells may be enzymatically dissociated, e.g., from culture plates or explant tissues. Upon enzymatic treatment, the cells typically to shrink to smaller balls. As a general guide, after enzymatic treatment animal cells are typically from several micrometers to 30 micrometers. For example, after trypsin treatment, cells of a porcine aortal endothelial cell line (PAEC cells) are about 10-20 μm.

In some embodiments, the orifice is between 10 and 200 μm in diameter, or between 20 and 100 μm in diameter, or between 30 and 70 μm. In further embodiments, the orifice is about 40 or 50 μm in diameter. A plurality of orifices with the same or different diameters may be provided. Though in some embodiments the orifices have a circular opening, other suitable shapes may be used, e.g., oval, square, rectangle, etc., without departing from the spirit of the invention.

Stated another way, in some embodiments the orifice is not more than 1, 1.5, 2, 3, 5, 8, 10 or 12 times greater than the average diameter of the cells to be transfected. In other embodiments, the orifice is the same size or smaller than the average diameter of the cells to be transfected, for example, ⅛, ¼, ½, ¾, or ⅞ the size of the average diameter of the cells to be transfected. Some embodiments include size ranges between ⅛ and 12 times the average diameter, or between ¼ and 10 times, or between ½ and 8 times the average diameter of the cells to be transfected.

In further embodiments, the cells may be exposed to high heat, e.g., greater than 50, 80, or 100 degrees Celsius. In other embodiments, the cells are exposed to heat greater than 120, 150, 180, or 200 degrees Celsius. In still other embodiments, the cells are exposed to heat greater than 220, 250, 280, or 300 degrees Celsius. For example, cells and/or compositions in which cells are included may be in contact with the heated plate of a printer head, which is heated in order to spray droplets of the cells/composition, as discussed below. In some embodiments, the cells are exposed to heat for a limited period of time e.g., from $10^{-5}$ to $10^{-7}$ seconds. In some embodiments, the limited period of time is from 0.5 to 10 microseconds.

According to some embodiments, at least a portion of the cells are transfected upon stressing and/or heating the cells in the presence of the compound of interest. The portion of viable cells transfected may be determined by calculating the percentage or rate of transfection of viable or adherent cells (e.g., calculated from the relation between GFP-positive or lacZ-positive cells and DAPI-positive cells, respectively). "Viable" as used herein includes cells that are adherent to a culture dish or other substrate and/or are capable of survival (e.g., proliferation). In some embodiments, at least 0.5, 1, or 2% of viable cells are transfected. In other embodiments, at least 3, 4 or 5% of viable cells are transfected. In still other embodiments, at least 6, 7, 8, 10 or 12% of viable cells are transfected. In further embodiments, at least 15, 20 or 30% or more of viable cells are transfected.

In addition, the total transfection rate may be determined by multiplying the transfection rate of viable or adherent cells with the viability of each culture sample (i.e., the percentage of total cells loaded that are viable after the transfection step). In some embodiments, at least 15, 20 or 25% of the total cells loaded are viable after transfecting at least a portion of the cells. In other embodiments, at least 30, 40 or 50% of the total cells provided are viable, and in further embodiments at least 60, 70, 80, or 90% or more of the total cells provided are viable after transfecting at least a portion of the cells. Cell viability may be measured by any conventional means, e.g., the MTS assay. The total transfection rate according to some embodiments is at least 1, 2, 4, or 8%, or at least 10, 15, 20, or 30% or more.

In some embodiments cells transfected with compounds of interest can be delivered into substrates, including 3D scaffolds, and facilitate the formation and functionalization of engineered tissues and organs. Examples of other applications include, but are not limited to, 2-dimentional or 3-dimentional arrays of cells transfected with at least one compound of interest.

Transfection by Inkjet Printing.

In some embodiments, cells are transfected by co-printing with compounds of interest. Methods and compositions for the inkjet printing of viable cells are known and described in, for example, U.S. Pat. No. 7,051,654 to Boland et al.; Wilson et al. (2003) The Anatomical Record Part A 272A: 491-496. The cells may also be printed by other means, such as the methods and compositions for forming three-dimensional structures by deposition of viable cells described in U.S. Pat. No. 6,986,739 to Warren et al.

Without wishing to be bound to any particular theory, it is hypothesized that the possible mechanism by which cells are transfected with inkjet printing involves the high shear stress (up to 10 $ms^{-1}$ in some embodiments), and/or high heat (up to 300 degrees Celsius in some embodiments) that can occur during the inkjet printing process, resulting in physicomechanical changes of the cellular membrane of the cells that facilitate the transfer of compounds of interest into the cells (FIG. 1).

Examples of cells that may be transfected by inkjet printing include both eukaryotic and prokaryotic cells, without limitation, as above. Examples of eukaryotic cells that may be transfected using the methods herein include, but are not limited to, mammalian cells, including stem cells, progenitor cells and differentiated cells. In some embodiments, transfection by inkjet printing is a comparatively mild transfection condition. As an illustration, in some embodiments a relatively high percentage of the cells are viable upon printing (e.g., 70, 80, or 90% or more). This may be particularly important for the transfection of more sensitive cells such as stem and progenitor cells. Progenitor cells are termed as undifferentiated cells with a high proliferation capacity, the capability of self-renewal, and the potential for multilineage differentiation. A major concern with progenitor cells in gene transfection is whether these cells can still maintain their stem cell or undifferentiated status after being transfected. The mild inkjet printing transfection could maintain this important state for progenitor cells.

As another example, recently we have found human amniotic fluid stem cells (AFS), after transfection with electroporation or liposome based agents, will stop growth, or even most of them went through apoptosis. In contrast, inkjet printing according to some embodiments of the present invention do not have significant effects on the viability, proliferation, and basic functions of the AFS stem cells.

In some embodiments, the cells and/or compounds of interest may be provided in a liquid carrier, as above. Concentrations of compounds of interest used according to some embodiments include, but are not limited to, from 0.01 to 50 µg/µL, 0.05 to 10, 15 or 20 µg/µL, 0.1 to 5 µg/µL, 0.1 to 2.0 µg/µL, and 1 to 2 µg/µL of the composition, as above. Concentrations of cells in the composition according to some embodiments include, but are not limited to, approximately $10^5$, $10^6$, $10^7$, $10^8$ or $10^9$ cells/mL.

The transfection may be carried out by stressing the cells, e.g., with tensile or shear stress, including compression or inertial loading or fluid movement that occurs during the inkjet printing. In some embodiments, the shear stress is from 0.5 to 500 $ms^{-1}$, or from 1 to 100 $ms^{-1}$, or from 5 and 15 $ms^{-1}$. See Okamoto et al. (2000) *Nature Biotechnology* 18:438-441.

In some embodiments, cells are exposed to high heat, e.g., greater than 50, 80, or 100 degrees Celsius. In other embodiments, the cells are exposed to heat greater than 120, 150, 180, or 200 degrees Celsius. In still other embodiments, the cells are exposed to heat greater than 220, 250, 280, or 300 degrees Celsius. In certain embodiments involving inkjet printing, the heat is created by a heated plate of a printer cartridge. In some embodiments, the cells are exposed to heat for a limited period of time e.g., from $10^{-5}$ to $10^{-7}$ seconds. In further embodiments, the limited period of time is from 0.5 to 10 microseconds. See Calvert (2001) *Chem. Mater.* 13:3299-3305.

In some embodiments, compounds of interest are transfected by inkjet printing with a modified inkjet printer. Modifications may include, but are not limited to, means to control the temperature, humidity, shear force, speed of printing, and firing frequency, by modifications of, e.g., the printer driver software and/or the physical makeup of the printer. See, e.g., Pardo et al. (2003) *Langmuir* 19:1462-1466; U.S. Pat. No. 7,051,654 to Boland et al. Not every modification suggested in these references will be suitable to a given application, as will be appreciated by those skilled in the art. For example, in some embodiments, printers were not modified using new gear mount pillars with closer tolerances by adding a horizontal support, changing the transistor in the circuit to one with higher amplification, and reentering the horizontal position encoder. Also, in some embodiments, printer software was not modified to lower the resistive voltages to avoid heating of the solutions above 37° C.

In some embodiments, printers (e.g., the commercial printers HP695C and HP550C) can be modified as follows. The printer top cover may be removed and the sensor for the cover disabled. The paper feeding mechanism may be disabled to allow printing of cells onto solid substrates (e.g., glass coverslips). The ink absorbing pads (on the right side of the HP695C and HP550C printers) may be removed (e.g., to avoid the pads contaminating the bottom of the print cartridges during the printing process). To offer the capability of the printer to print 3D constructs, a customized z-axis module with a controlled elevator chamber may be added to the modified printers.

During the nozzle firing in the print head, compounds of interest can be transferred into living cells. The "print head" is the device in an inkjet printer that sprays droplets (e.g., ink). In some embodiments, the compounds of interest are loaded into the ink cartridges together with the cells intended to be transfected. In other embodiments, cells are premixed with compounds of interest before loading. In still other embodiments, cells and compounds of interest are loaded sequentially, such that the loaded composition contains both cells and compounds of interest.

In some embodiments, the inkjet printing device is a thermal bubble inkjet printer. In general, in a thermal bubble inkjet printer, resistors create heat in the print head, which vaporizes ink to create a bubble. As the bubble expands, some of the ink is pushed out of a nozzle onto the paper. A vacuum is created when the bubble collapses, which pulls more ink into the print head from the cartridge. In the present invention, the ink is replaced with, e.g., cells and/or compounds of interest (e.g., in a liquid carrier), and the paper is replaced with a suitable substrate, e.g., an agar or collagen coated substrate. See, e.g., U.S. Pat. No. 6,537,567 to Niklasen et al.

In some embodiments, compounds of interest are transfected by printing with an inkjet print head (e.g., 51626a or 51629a, Hewlett Packard, Palo Alto, Calif.) onto a substrate (e.g., a tissue or scaffold). In some embodiments the print head has a face plate with a plurality of rows and/or nozzles. In certain embodiments, the face plate has two rows of 25 orifices or nozzles.

In some embodiments, the nozzle is between 0.05 and 200 µm in diameter, or between 0.5 and 100 µm in diameter, or between 10 and 70 µm, or between 20 and 60 µm in diameter. In further embodiments, the nozzle is about 40 or 50 µm in diameter. A plurality of nozzles with the same or different diameters may be provided. Though in some embodiments the nozzles have a circular opening, other suitable shapes may be used, e.g., oval, square, rectangle, etc., without departing from the spirit of the invention, taking into account the relative size of the cells intended to be transfected. As a general guide, eukaryotic animal cells and plant cells are typically from 10 to 100 µm, and prokaryotic cells are typically from 0.1 to 10 µm in diameter. Before printing, in some embodiments the cells may be enzymatically dissociated, e.g., from culture plates or explant tissues. Upon enzymatic treatment, the cells typically to shrink to smaller balls. As a general guide, after enzymatic treatment animal cells are typically from several micrometers to 30 micrometers. For example, after trypsin treatment, cells of a porcine aortal endothelial cell line (PAEC cells) are about 10-20 µm.

Stated another way, in some embodiments the orifice is not more than 1.5, 2, 3, 5, 7, 10, 15 or 20 times greater than the average diameter of the cells to be transfected. As an example, the nozzles of the HP 51629a and HP 51626a cartridges are about 40 and 50 micrometers, respectively (see Xu et al. (2006) *Biomaterials* 27(19):3580-88). Therefore, in some embodiments the relative nozzle size is between 1.3 and 10 times the diameter of the cells being transfected. In further embodiments, the relative nozzle size is between 0.8 and 20 times the diameter of the cells being transfected.

In other embodiments, the orifice is about the same size or smaller than the average diameter of the cells to be transfected, for example, ⅛, ¼, ½, ¾ or ⅞ the size of the average diameter of the cells to be transfected. Some embodiments include size ranges between ⅛ and 12 times the average diameter, or between ¼ and 10 times, or between ½ and 8 times the average diameter of the cells to be transfected.

In some embodiments, each orifice is linked with a separate chamber in the print head. According to some embodiments, during the printing process individual cells with the loaded compound of interest may go through only one of a plurality of nozzles and chambers, and transfection may be performed within any one of the nozzles. In some embodiments, the print head is capable of printing more than 250,000 drops per second, providing methods for high-throughput gene transfection.

In other embodiments, compounds of interest are transfected by printing with a piezoelectric crystal vibration print head. In general, a piezoelectric crystal receives an electric charge that causes it to vibrate, forcing ink out of the nozzle, and pulling more ink into the reservoir. In the present invention, the ink is replaced with, e.g., cells and/or a compound of interest in aqueous solution. Compared with the thermal inkjet printing, the piezo-based inkjet printing usually requires more power and higher vibration frequencies. Typical commercial piezo-printers use frequencies up to 30 kHz and power sources ranging from 12 to 100 W. Vibrating frequencies ranging from 15 to 25 kHz and power sources from 10 to 375 W are often used to disrupt cell membranes. (See Xu et al. (2005) *Biomaterials* 26: 93-99). Therefore, in some embodiments a piezoelectric crystal vibration print head is used, with a vibrating frequency of 1, 5, 10 or 15, to 20, 25, 30, or 35 or more kHz, and power sources from 5, 10, 20, 50, 100, 120, or 150, to 200, 250, 300, 350, or 375 or more Watts.

According to some embodiments, at least a portion of viable cells are transfected upon co-printing with compounds of interest. The portion of viable cells transfected may be determined by calculating the percentage or rate of transfection of viable or adherent cells (e.g., calculated from the relation between GFP-positive or lacZ-positive cells and DAPI-positive cells, respectively). "Viable cells" includes cells that adherent to a culture dish or other substrate and/or are capable of survival (e.g., proliferation). In some embodiments, at least 0.5, 1, or 2% of viable cells are transfected. In other embodiments, at least 3, 4 or 5% of viable cells are transfected. In still other embodiments, at least 6, 7, 8, 10 or 12% of viable cells are transfected. In further embodiments, at least 15, 20 or 30% or more of viable cells are transfected. In addition, the total transfection rate may be determined by multiplying the transfection rate of viable or adherent cells with the viability of each culture sample, as above. In some embodiments, at least 15, 20 or 25% of the total cells loaded are viable after transfection of at least a portion of the cells. In other embodiments, at least 30, 40 or 50% of the total cells loaded are viable, and in further embodiments at least 60, 70, 80, or 90% or more of the total cells loaded are viable after transfection of at least a portion of the cells. Cell viability may be measured by any conventional means, e.g., the MTS assay. The total transfection rate according to some embodiments is at least 1, 2, 4, or 8%, or at least 10, 15, 20, 30% or more.

Various mechanisms may be employed to facilitate the survival of the cells during and/or after printing. Specifically, compounds may be utilized that support the printed cells by providing hydration, nutrients, and/or structural support. These compounds may be applied to the substrate using conventional techniques, such as manually, in a wash or bath, through vapor deposition (e.g., physical or chemical vapor deposition), etc. These compounds may also be combined with the cell composition before and/or during printing, or may be printed or otherwise applied to the substrate (e.g., coated) as a separate layer beneath, above, and/or between cell layers. For example, one such support compound is a gel having a viscosity that is low enough under the printing conditions to pass through the nozzle of the print head, and that can gel to a stable shape during and/or after printing. Such viscosities are typically within the range of from about 0.5 to about 50 centipoise, in some embodiments from about 1 to about 20 centipoise, and in some embodiments, from about 1 to about 10 centipoise. Some examples of suitable gels that may be used in the present invention include, but are not limited to, agars, collagen, hydrogels, etc.

Besides gels, other support compounds may also be utilized in the present invention. Extracellular matrix analogs, for example, may be combined with support gels to optimize or functionalize the gel. In some embodiments, one or more growth factors may also be introduced in the printed arrays. For example, slow release microspheres that contain one or more growth factors in various concentrations and sequences may be combined with the cell composition and/or compound of interest composition to accelerate and direct the cell fusion process. Other suitable support compounds might include those that aid in avoiding apoptosis and necrosis of the developing structures. For example, survival factors (e.g., basic fibroblast growth factor) may be added. In addition, transient genetic modifications of cells having antiapoptotic (e.g., bcl-2 and telomerase) and/or blocking pathways may be included in compositions printed. Adhesives may also be utilized to assist in the survival of the cells after printing. For instance, soft tissue adhesives, such a cyanoacrylate esters, fibrin sealant, and/or gelatin-resorcinol-formaldehyde glues, may be utilized to inhibit nascent constructs from being washed off or moved following the printing of a layer. In addition, adhesives, such as arginine-glycine-aspartic acid (RGD) ligands, may enhance the adhesion of cells to a gelling polymer or other support compound. In addition, extracellular proteins, extracellular protein analogs, etc., may also be utilized.

"Growth factor" as used herein may be any naturally occurring or synthetic growth factor, including combinations thereof, suitable for the particular tissue or array being printed. Numerous growth factors are known to those skilled in the art. Examples include, but are not limited to, insulin-like growth factor (e.g., IGF-1), transforming growth factor-beta (TGF-beta), bone-morphogenetic protein, fibroblast growth factor, platelet derived growth factor (PDGF), vascular endothelial growth factor (VEGF), connective tissue growth factor (CTGF), basic fibroblast growth factor (bFGF), epidermal growth factor, fibroblast growth factor (FGF) (numbers 1, 2 and 3), osteopontin, bone morphogenetic protein-2, growth hormones such as somatotropin, cellular attractants and attachment agents, etc., and mixtures thereof. See, e.g., U.S. Pat. Nos. 7,019,192; 6,995,013; and 6,923,833. For example, growth factor proteins may be provided in the printed composition and/or encoded by plasmids transfected into printed cells.

In some embodiments, compounds of interest, cells, support compounds, and/or growth factors may be printed from separate nozzles or through the same nozzle in a common composition, depending upon the particular tissue (or tissue substitute) being formed. Printing may be simultaneous, sequential, or any combination thereof. Some of the ingredients may be printed in the form of a first pattern (e.g., an erodable or degradable support material), and some of the ingredients may be printed in the form of a second pattern (e.g., cells in a pattern different from the support, or two different cell types in a different pattern). The particular combination and manner of printing will depend upon the particular tissue being printed.

Cells transfected according to the present invention may be used for, e.g., tissue engineering applications. In some embodiments, cells and compounds of interest are printed onto a substrate, e.g., a biocompatible scaffold, which may be subsequently implanted into a subject in need thereof. In other embodiments, cells and compounds of interest are directly printed in vivo onto living tissues in the body, with or without prior substrate application (e.g., a layer of fibrin) in which the cells may attach.

The present invention is explained in greater detail in the following non-limiting examples.

EXAMPLES

Here we report a novel and versatile method of gene transfection of living mammalian cells by using the inkjet printing method. We hypothesize the genes of interest can be effectively delivered into the living cells when they are co-printed through the firing inkjet nozzles, and the introduced genes can be expressed both in vitro and in vivo. Moreover, the cells can be delivered to pre-allocated target sites by the inkjet printer during the transfection process.

A possible mechanism of the transfection is shown in FIG. 1. Without wishing to be bound to any particular theory, it is thought that when cells and plasmids pass the ink channels of the printhead during the printing process, the high shear stress and/or heat occurring upon the nozzles firing may cause temporary micro-disruption of the cell membrane, allowing the plasmids to be transferred into the cells.

Example 1

In Vitro Transfection by Coprinting

A porcine aortal endothelial cell line (PAEC) was used, which was established previously in our lab by enzymatic dispersion of adult pig aorta, and the passage 15, 16 and 17 of the cell line were used for gene transfection. PAEC cells were maintained in F12 medium (GIBCO, Invitrogen, Carlsbad, Calif.) supplemented with 10% fetal bovine serum (GIBCO), and 100 IU penicillin and 100 mg/ml streptomycin at 37° C. in a humidified 5% $CO_2$ (95% air) atmosphere.

Cytomegalovirus (CMV) early immediate promoter driven plasmids encoding the cDNAs were used. The pmaxGFP™ (Amaxa GmbH, Germany, and Gaithersburg, Md.), pIRES-VEGF-GFP (BD Biosciences, Bedford, Mass.), and pIRES-lacZ (BCCM/LMBP, Belgium) plasmids were each amplified in DH5α strain of Escherichia coli, isolated by alkaline lysis, and purified by ion exchange column chromatography (Qiagen Inc., Valencia, Calif.). The pmaxGFP™ plasmid encodes the green fluorescent protein (GFP) from the copepod Potellina p.

For gene transfection we used modified commercial HP Desktop (695C and 550C) printers and ink cartridges (HP 51629a or 51626a). Briefly, the printer top cover was removed and the sensor for the cover was disabled. The paper feeding mechanism was also disabled to allow printing of cells onto the solid substrates, such as glass coverslips. The ink absorbing pads on the right side of the printer were taken out to avoid the pads contaminating the bottom of the print cartridges during the printing process. To offer the capability of the printer to print 3D constructs, a customized z-axis module with a controlled elevator chamber was added to the modified printers. The printers used a printer driver to allow different viscosities of solution to be printed. The printer drivers constantly adjusted the voltages to the nozzles to account for different impedances of the solutions, allowing the appropriate amount of solution to be dispensed. See also Pardo et al. (2003) Langmuir 19:1462-1466); U.S. Pat. No. 7,051,654 to Boland et al. (Note that not all of the modifications found in the Pardo et al. and Boland et al. references were used, e.g., the printers were not modified by using new gear mount pillars with closer tolerances by adding a horizontal position encoder, and resistive voltages were not lowered to avoid heating of the solution to above 37° C.)

The cartridges were rinsed thoroughly with ethanol and sterile water prior to cell print suspension introduction. A pattern of a square was designed using Microsoft PowerPoint to program the printer. The substrates were prepared from rat-tail Type I collagen gels by using the previously reported protocol (Shea et al. (1999) Nat Biotechnol 17, 551-554). After trypsinizing, PAEC cell pellets were collected and re-suspended in the Nucleofector™ solution (Amaxa) at a concentration of 1.5–2×10$^6$ cells/ml. The plasmids were added into the cell suspension in concentrations ranging from 0.1 µg/µl to 2 µg/µl.

The print suspensions containing the PAEC cells and plasmid genes were loaded into the ink cartridges. Upon the firing of the nozzles, the cell and plasmid mixture was printed onto the collagen gel coated substrates. After a 30 min incubation at 37° C. in a humidified 5% $CO_2$ (95% air) atmosphere, the culture medium was carefully added to the dishes to avoid disturbing the printed cell patterns. As a control, the PAEC cells and plasmids were mixed together and manually seeded onto the collagen gel coated substrates. They maintained the same cell density and concentration of the plasmid genes as the printed group. The gene transfection and growth of the cells were monitored daily via light and fluorescent microscopy.

Figure 2A:
FIGS. 2A-2H. In vitro inkjet transfection of the cells with pmaxGFP plasmids by co-printing with a modified commercial inkjet printer.
Figure 2B:
Figure 2C:
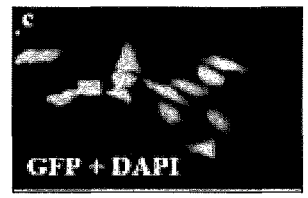

We found after 5-7 hours the printed cells began expressing GFP. Green fluorescence was clearly observed in the culture, and the strong GFP expression was continuously seen over a 10-day period (FIGS. 2A-C). However, no, or little if any, GFP gene expression was seen in the non-printed control group.

Example 2

Comparison with Common Transfection Methods

We further compared the cell viability and the transfection efficiency of the inkjet printing method with other chemical and physical transfection methods commonly used in tissue engineering. For this purpose, a common liposome based agent and an electroporation approach were performed. Lipofectamine™ 2000 (Invitrogen), a common liposome based agent, and Nucleofection, an electroporation approach, were compared to the printing method using the PAEC cell cultures.

For transfection with Lipofectamine™ reagent, PAEC cells were seeded in a 24-well plate at a density of 2×10$^5$ cells per well the day before transfection. Transfection was performed according to the manufacturer's protocol. Briefly, 0.8 µg pmaxGFP™ (Amaxa) and the equivalent amount of Lipofectamine™ 2000 reagent were each added to 50 µl of serum free F12 medium. After incubation for 5 min at room temperature (RT), they were mixed and further incubated for 20 min at room temperature (RT). The DNA/liposome complex was added to the 24-well plate and maintained up to 48 hours.

In the Nucleofection experiment, the Basic Nucleofector™ Kit for Primary Mammalian Endothelial Cells (Amaxa) was used. In order to help the customers to use the product of the Basic Nucleofector™ Kit more effectively, the vendor (Amaxa) has tested cells and set up a database containing programs to aid in the use of the transfection kit. The programs of W-023 and Y-022 are included in the database and specially designed for primary mammalian endothelial cells. The cells used for the inkjet printing in these experiments are also mammalian endothelial cells. Both of these programs were designed for transfection of primary endothelial cells from porcine aorta.

Program W-023 showed better results in viability and transfection efficiency for the PAEC cells, and was used for further experiments. The transfection was performed according to the manufacturer's protocol for endothelial cells. After trypsinization, the detached cells were adjusted to the volume of $5 \times 10^5$ in the culture medium. Afterwards, the cells were centrifuged, and medium was removed. The cells were re-suspended in 100 μl of Nucleofector™ solution with 3 μg of plasmid DNA. After the electrical pulse, 500 μl of F12 medium (Gibco) containing 10% FBS was immediately added to neutralize the Nucleofector™ solution. Cells had been seeded on 6 cm dishes with pre-warmed culture medium and incubated in a humidified 37° C./5% $CO_2$ incubator (95% air) for 24 hours before further analyses.

For each gene transfection method, cell viability was evaluated after transfection by using the tetrazolium compound (MTS) assay (Sigma-Aldrich) according to the manufacturer's protocol. Briefly, 500 ml of reagent was added per ml of media into the transfected samples and non-transfected samples. In individual transfection experiments, the transfected samples were prepared using the transfection methods described above, and in order to estimate the total cell number, the non-transfected samples were also prepared using the same conditions as the transfected samples, except they did not experience the transfection process. After the samples were incubated for 2 hours in the dark at RT, the absorbance at 540 nm was measured using a spectrophotometer. The percentages of cells lysed in the 3 different transfection methods were estimated as the relationships between the absorbance of the transfected samples to those of the non-transfected samples.

After 24-48 hours of culture, the transfected samples were thoroughly washed with PBS to remove the lysed or non-adherent cells, and then fixed with 4% paraformaldehyde solution. DAPI staining (10 mg/ml) was used to evaluate the total number of the viable cells in the culture. For the transfection with the GFP, including pmaxGFP™ and VEGF-GFP plasmids, the GFP-positive green fluorescent cells were counted to measure the transfection rate. For the transfection with the lacZ, cellular β-galactosidase activity was assessed by X-gal staining (Boehringer Mannheim, Indianapolis, Ind.), and the cells expressing the lacZ gene were stained in blue. The lacZ-positive blue stained cells were counted to estimate the transfection rate. Cells were counted at 10× magnification using an inverse Zeiss fluorescent microscope (Carl Zeiss, Inc., Thornwood, N.Y.). Four fields were randomly selected in every well, and at least 4-6 wells were counted for each sample. The transfection rate of viable cells was calculated from the relation between GFP-positive or lacZ-positive cells and DAPI-positive cells. The total transfection rate was estimated by multiplying the transfection rate of viable cells with the viability of each culture sample.

Figure 2D:
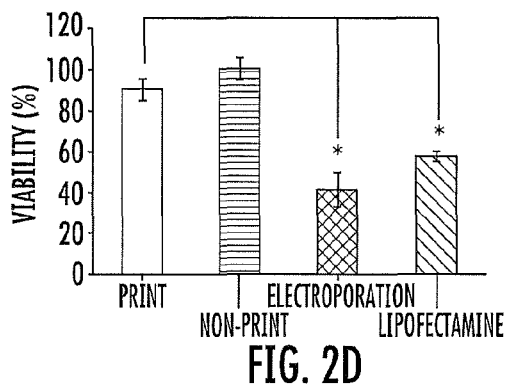

Compared to the two common chemical and physical methods, the inkjet method exhibited significantly higher cell viability after printing and transfection of the living cells (FIG. 2D). As many as over 90% of the cells were not lysed during the printing and transfection process. This concurs with previously reported viability results (see Xu et al. (2005) *Biomaterials* 26, 93-99; Nakamura et al. (2005) *Tissue Eng* 11, 1658-1666) and also reconfirms that the inkjet printing process is a mild treatment causing minimal damage to the printed cells (Xu et al. (2006) *Biomaterials* 27, 3580-3588).

Figure 3:
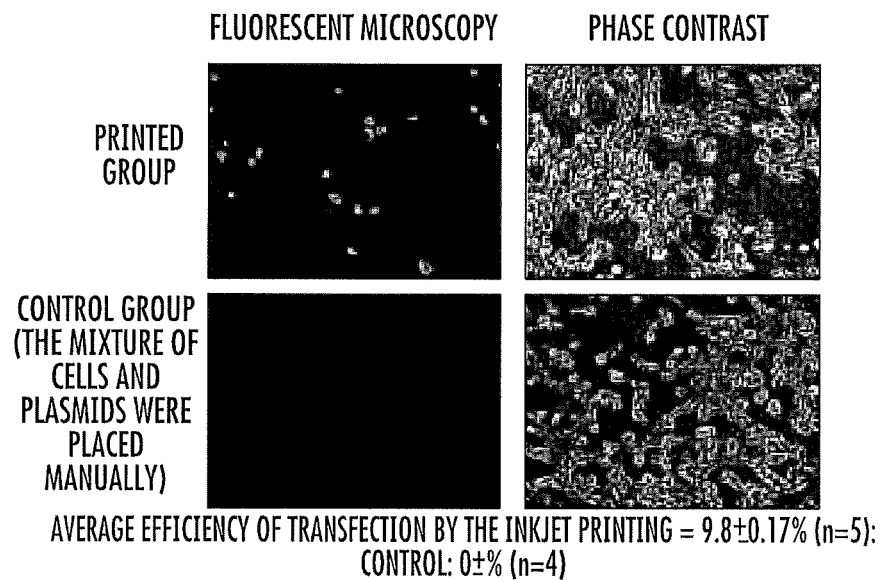
FIG. 3. Fluorescent microscopy and phase contrast images of a group of cells printed with pmaxGFP™ plasmid at Day 1 (HP695C printer). In the control group the mixture of cells and plasmids were placed manually.
Figure 4:
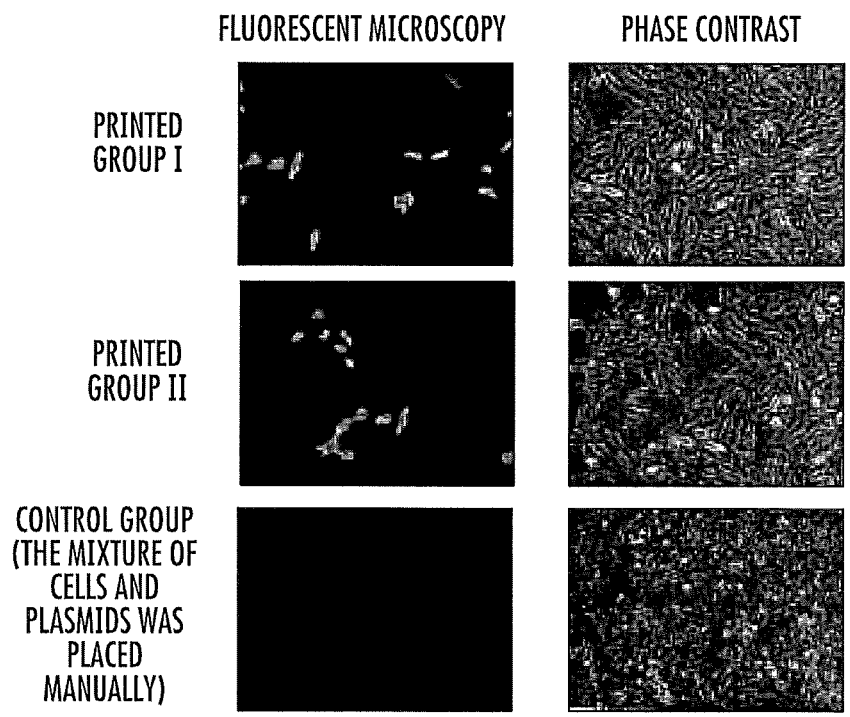
FIG. 4. Fluorescent microscopy and phase contrast images of two groups of cells printed with pmaxGFP™ plasmid at Day 2 (HP550C printer). In the control group the mixture of cells and plasmids were placed manually.
Figure 5:
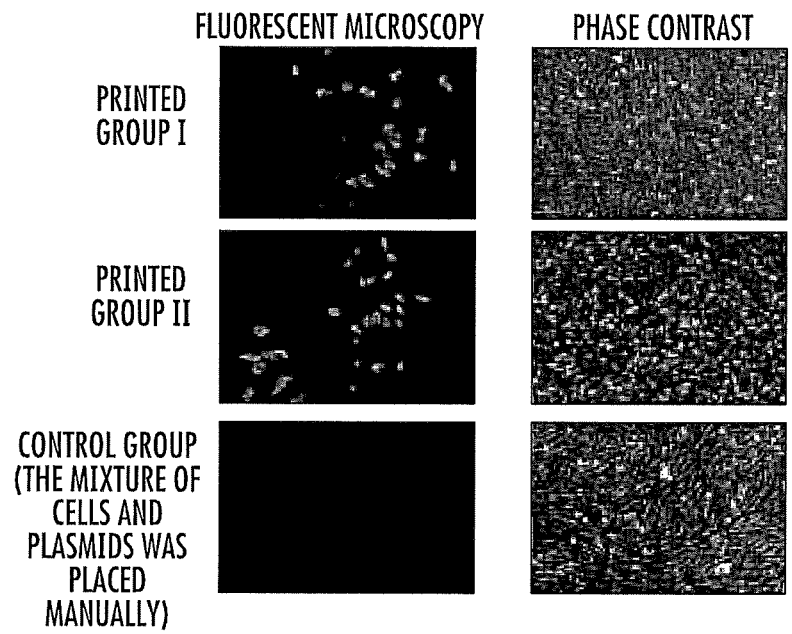
FIG. 5. Fluorescent microscopy and phase contrast images of two groups of cells printed with pmaxGFP™ plasmid at Day 4 (HP550C printer). In the control group the mixture of cells and plasmids were placed manually.
Figure 6:
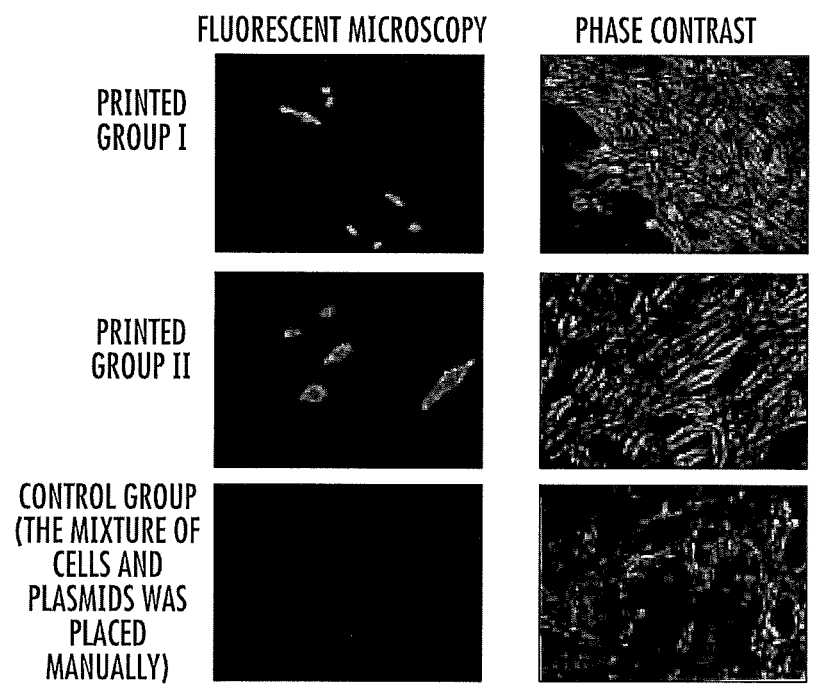
FIG. 6. Fluorescent microscopy and phase contrast images of two groups of cells printed with GPF and VEGF at Day 2 (HP550C printer). In the control group the mixture of cells and plasmids were placed manually.

After 1 day of culture, the living cells plus pmaxGFP™ printed with the HP695C printer exhibited green color under the fluorescent microscope, indicating that during the printing process the GFP genes were effectively expressed within the printed cells (FIG. 3). Cells plus pmaxGFP™ plasmid (Amaxa Biosystems, Gaithersburg, Md.) printed with the HP550C printer also showed GFP expression at day 2 (FIG. 4) and day 4 (FIG. 5). Cells plus plasmids encoding GFP and VEGF printed with the HP550C printer showed GFP expression at day 2 (FIG. 6).

In the transfection process, some cells are lysed (dead), and most of these dead cells do not adhere to the culture plates and can be washed out from the culture plate. To evaluate the transfection rate, the transfected samples were thoroughly washed with PBS to remove the lysed cells. In a given plate, the number of the total cells after the washing procedure was counted as $N_C$ (this number should be close to, but not equal to the number of the viable cells, because dead cells cannot be washed out 100%, and a few of the live cells can be washed out). The number of transfected cells (e.g., positive for GFP) was counted as $N_T$. The transfection rate of the viable cells means the percentage of the transfected cells to the viable cells in the plate. Transfection rate of the viable cells=$N_T/N_C$. The total transfection rate means the percentage of the transfected cells to the total cells, which are initially printed onto the substrates (the plates). The total transfection rate=the transfection rate of the viable cells×viability (%).

Figure 2E:
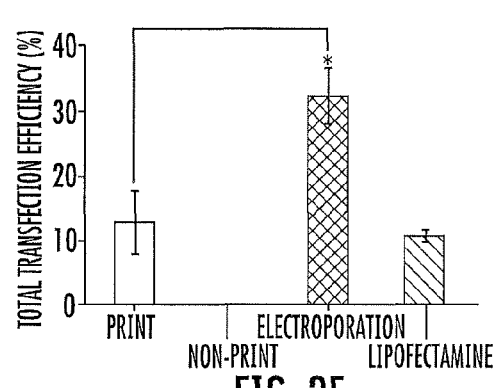

We found that as many as 12% of the printed cells had been transfected with the plasmid gene. The inkjet gene transfection data suggest that the inkjet printing process, involving heat and shear shocks, facilitated entry of the plasmids into the printed cells. However, the exact mechanism associated with the inkjet transfection method needs further investigation. As shown in FIG. 2E, the total efficiency of the inkjet transfection method to transfect with pmaxGFP™ was significantly smaller than the electroporation-based method, but higher than the liposome-based method.

Example 3

Comparison of Ink Cartridges, Concentration and Size of Plasmid

Figure 2F:
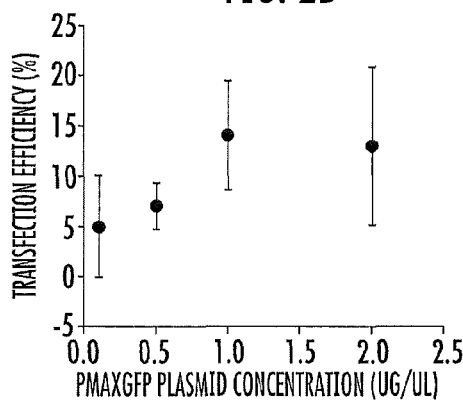
Figure 2G:
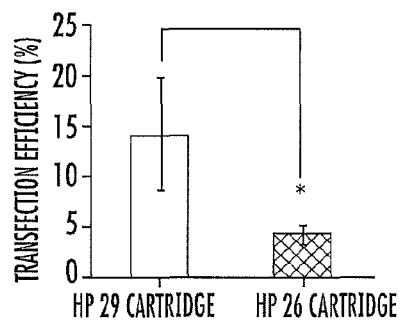

Different HP cartridges were also tested for inkjet gene transfection. The HP 51629a cartridge demonstrated higher gene transfection efficiency than the HP 51626a cartridge, as shown in FIG. 2G. The HP 51629a and HP 51626a cartridges share many similar printing parameters and mechanisms, but differ in the nozzle size. It is believed that the HP 51629a cartridge has a relatively smaller nozzle diameter than the HP 51626a cartridge, which may cause the higher stress, thus leading to higher transfection efficiency. After trypsin treatment, PAEC cells are about 10-20 μm. The nozzles of the HP 51629a and HP 51626a cartridges are about 40 and 50 micrometers, respectively (see Xu et al., *Biomaterials* (2006) 27(19):3580-88).

It was also found that several other factors could affect the transfection. Different concentrations of the plasmids in the print suspension were tested. As shown in FIG. 2F, the gene expression levels of the pmaxGFP™ at its higher concentrations (1.0 µg/µl and 2.0 µg/µl) were significantly higher than at its lower concentrations (0.1 µg/µl and 0.5 µg/µl). This may result from the higher possibility of the plasmids' proximity to the cell membrane and entry into the cells when there is a higher ratio of the gene plasmid in the ink channels during the nozzle firing.

Figure 2H:
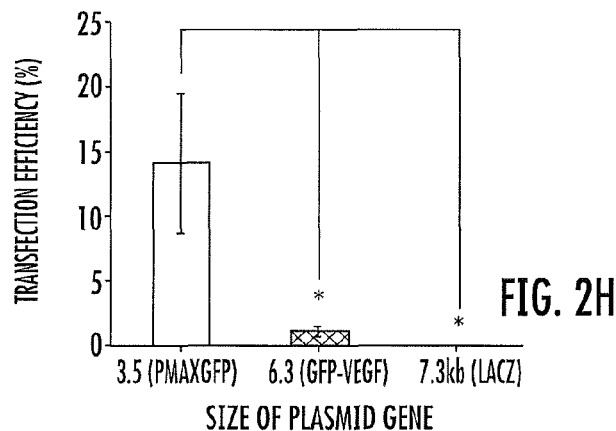

Furthermore, plasmids of different sizes were also tested. It was seen that the pmaxGFP™ plasmid with a relatively smaller size (3.2 kb) had a higher transfection efficiency that the other two plasmids (pIRES-VEGF-GFP and pIRES-lacZ) that were relatively larger (FIG. 2H). The possible reason is that the inkjet printing conditions with relatively lower powers in this study can only open smaller micropores in the cell membrane, and it is difficult for the larger gene plasmids to enter into the cells. In order to transfect with the larger plasmid gene, specific printing parameters and conditions, such as temperature, firing frequency, and structural design of the cartridge ink channel may need to be further optimized.

Example 4

In Vivo Inkjet Gene Transfection

To evaluate whether the inkjet gene transfection can be performed in vivo, fibrin gel was directly printed into nude mouse subcutaneous tissues, and then the PAEC cells together with the pmaxGFP™ plasmids were directly printed on the pre-formed fibrin gel. To differentiate the graft cells from the native cells within the host animal, the PAEC cells were labeled with PKH67 red fluorescent dyes (Sigma-Aldrich, St. Louis, Mo.). All animal experiments were performed according to ACUC protocols at Wake Forest University Health Sciences.

PAEC cells were trypsinized and washed with serum-free DMEM. The cells were suspended in $2\times10^{-6}$ mM PKH67 solution of diluent C (Sigma-Aldrich, St. Louis, Mo.) at the concentration of $1\times10^7$ cells/ml, and incubated for 4 min at room temperature. The staining reactions were quenched with the addition of an equal volume of DMEM supplemented with 10% FBS and washed. After being cultured overnight under the medium, the PKH67 labeled PAEC cells are ready for the in vivo direct printing described below.

The ability of the in vivo gene transfection induced by the inkjet printing was assessed by direct printing of the PAEC cells with plasmid DNA into subcutaneous tissues of athymic mice. Before printing, the cells were labeled with PKH67 florescent dye as described above for determination of the location of the grafted (printed) cells inside the host. Fibrinogen (20 mg/ml dissolved in PBS) (Sigma) and thrombin (20 IU/ml in 40 mM $CaCl_2$) (Sigma) were alternately printed into the mice subcutaneous tissues to generate a fibrin gel scaffold, and then the PAEC cells and pmaxGFP™ plasmids were co-printed on the fibrin gel. This procedure was repeated twice, resulting in a 3D fibrin sheet with a certain structure that contained the transfected cells. After 1 week of implantation, the in vivo printed fibrin sheet was retrieved and immediately examined under a fluorescent microscope.

Figure 7A:
FIGS. 7A-7D. In situ direct printing and in vivo inkjet gene transfection.
Figure 7B:
Figure 7C:
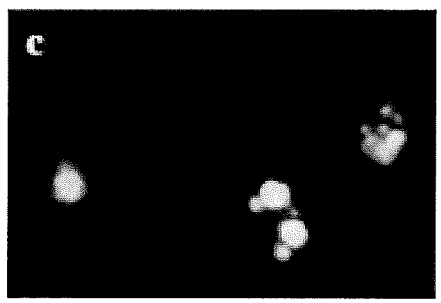
Figure 7D:
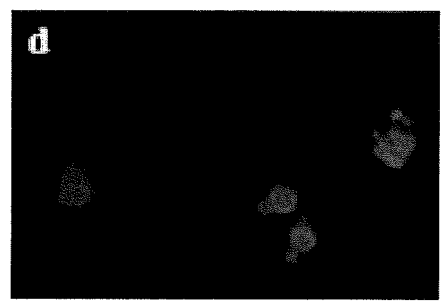

After in vivo direct printing, a 3D fibrin gel with a certain structure was formed in situ directly under the mouse subcutaneous tissues, as shown in FIGS. 7A and 7B. The printed cells expressed the GFP genes were clearly seen within the fibrin gel under green fluorescent microscopy (excitation 488 nm; emission 515-545 nm) (FIG. 7C). Furthermore, the cells were also seen in red under red fluorescent microscopy (excitation 560 nm; emission 583 nm) (FIG. 7D), to confirm the GFP transfected cells were not from the native tissues but from the graft cells delivered by the inkjet printer.

This study shows the exciting adaptation of the inkjet technology to accomplish transfection for tissue engineering applications. In addition to having the ability to precisely deliver cell populations to their target sites, inkjet printing can also aid in specific function and effects on the living cells. Genes of interest can be delivered into the cells, and the cells can express the genes both in vitro and in vivo. Furthermore, the in situ fabrication by using the inkjet method and the in vivo direct printing as demonstrated in this study may offer the possibility of fabricating within the body specific cell reservoirs in which the transfected cells are located with correct spatial registrations, and produce the continuous and controlled growth factors needed for tissue formation and regeneration.

The foregoing is illustrative of the present invention, and is not to be construed as limiting thereof. The invention is defined by the following claims, with equivalents of the claims to be included therein.

That which is claimed is:

1. A method for transfecting cells with a compound of interest, wherein at least a portion of said cells are transfected with said compound of interest, said method comprising the steps of:
   providing a composition comprising said cells in the presence of said compound of interest in a liquid carrier; and then
   forcing said composition through an orifice so that said cells are stressed in the presence of said compound of interest, wherein said orifice has a diameter of between one-eighth and twelve times the average diameter of said cells, and wherein said cells are stressed for a period of from 0.1 to 10 microseconds;
   thereby transfecting at least a portion of said cells with said compound of interest,
   wherein said forcing step is carried out by inkjet printing of said cells with an inkjet printing device.

2. The method of claim 1, wherein said inkjet printing device is selected from the group consisting of thermal inkjet printers and piezoelectric inkjet printers.

3. The method of claim 1, wherein said inkjet printing device comprises at least one inkjet cartridge, and wherein said inkjet cartridge is selected from the group consisting of thermal inkjet printer cartridges and piezoelectric inkjet printer cartridges.

4. A method of printing cells, wherein at least a portion of said cells are transfected with a compound of interest, said method comprising the steps of:
   providing an inkjet printing device, said device comprising at least one inkjet printer cartridge;
   loading a composition to be printed into said printer cartridge, such that said composition upon loading comprises said cells in the presence of said compound of interest; and
   printing said composition onto a substrate, wherein said cells are printed through an orifice having a diameter of between one-eighth and twelve times the average diameter of said cells, and wherein said cells are stressed for a period of from 0.1 to 10 microseconds during said printing;

thereby transfecting at least a portion of said cells with said compound of interest.

5. The method of claim 4, wherein said substrate of said printing step is coated with collagen.

6. The method of claim 4, wherein said printing step is carried out by printing said composition onto a tissue substrate in vivo.

7. The method of claim 4, wherein said at least a portion of said cells is at least 1% of cells that are viable after said printing step.

8. The method of claim 4, wherein said at least a portion of said cells is at least 5% of cells that are viable after said printing step.

9. The method of claim 4, wherein said at least a portion of said cells is at least 10% of cells that are viable after said printing step.

10. The method of claim 4, wherein at least 25% of the cells in said loading step are viable after said forcing step.

11. The method of claim 4, wherein at least 50% of the cells in said loading step are viable after said forcing step.

12. The method of claim 4, wherein at least 75% of the cells in said loading step are viable after said forcing step.

13. The method of claim 4, wherein said printer cartridge of said providing step comprises a plurality of nozzles, and wherein said nozzles have a diameter of from 0.01 to 100 micrometers.

14. The method of claim 4, wherein said cells of said loading step are eukaryotic cells.

15. The method of claim 4, wherein said cells of said loading step are prokaryotic cells.

16. The method of claim 4, wherein said compound of interest of said loading step is selected from the group consisting of: nucleic acids, proteins, molecules, nanoparticles and drugs.

17. The method of claim 4, wherein said compound of interest of said loading step comprises a nucleic acid.

18. The method of claim 4, wherein said composition of said loading step is premixed.

19. The method of claim 4, wherein said inkjet printing device of said providing step is selected from the group consisting of thermal inkjet printers and piezoelectric inkjet printers.

20. The method of claim 4, wherein said inkjet printer cartridge of said providing step is selected from the group consisting of thermal inkjet printer cartridges and piezoelectric inkjet printer cartridges.

21. A method of forming an array of viable cells wherein at least a portion of said cells are transfected with at least one compound of interest, said method comprising the steps of:
   providing an inkjet printing device, said device comprising at least one inkjet printer cartridge;
   loading a composition to be printed into said printer cartridge, such that said composition upon loading comprises cells in the presence of at least one compound of interest; and
   printing said composition onto a substrate in an organized pattern, wherein said cells are printed through an orifice having a diameter of between one-eighth and twelve times the average diameter of said cells, and wherein said cells are stressed for a period of from 0.1 to 10 microseconds during said printing;
   thereby forming an array of viable cells wherein at least a portion of said cells are transfected with said at least one compound of interest.

22. The method of claim 21, wherein said substrate of said printing step is coated with collagen.

23. The method of claim 21, wherein said printing step is carried out by printing said composition onto a tissue substrate in vivo.

24. The method of claim 21, wherein said at least a portion of said cells is at least 1% of cells that are viable after said printing step.

25. The method of claim 21, wherein said at least a portion of said cells is at least 5% of cells that are viable after said printing step.

26. The method of claim 21, wherein said at least a portion of said cells is at least 10% of cells that are viable after said printing step.

27. The method of claim 21, wherein at least 25% of the cells in said loading step are viable after said printing step.

28. The method of claim 21, wherein at least 50% of the cells in said loading step are viable after said printing step.

29. The method of claim 21, wherein at least 75% of the cells in said loading step are viable after said printing step.

30. The method of claim 21, wherein said printer cartridge of said providing step comprises a plurality of nozzles, and wherein said nozzles have a diameter of from 0.01 to 100 micrometers.

31. The method of claim 21, wherein said cells of said loading step are eukaryotic cells.

32. The method of claim 21, wherein said cells of said loading step are prokaryotic cells.

33. The method of claim 21, wherein said compound of interest of said loading step is selected from the group consisting of: nucleic acids, proteins, molecules, nanoparticles and drugs.

34. The method of claim 21, wherein said compound of interest of said loading step comprises a nucleic acid.

35. The method of claim 21, wherein said composition of said loading step is premixed.

36. The method of claim 21, wherein said inkjet printing device of said providing step is selected from the group consisting of thermal inkjet printers and piezoelectric inkjet printers.

37. The method of claim 21, wherein said inkjet printer cartridge of said providing step is selected from the group consisting of thermal inkjet printer cartridges and piezoelectric inkjet printer cartridges.

* * * * *